United States Patent

Suyama et al.

Patent Number: 5,292,914
Date of Patent: Mar. 8, 1994

[54] ORGANIC PEROXIDE AND USE THEREOF

[75] Inventors: Shuji Suyama; Tomoyuki Nakamura; Hiroyuki Nagai, all of Aichi; Mieko Takei, Handa, all of Japan

[73] Assignee: NOF Corporation, Tokyo, Japan

[21] Appl. No.: 84,174

[22] Filed: Jul. 1, 1993

[30] Foreign Application Priority Data

Jul. 28, 1992 [JP] Japan .................. 4-219611

[51] Int. Cl.$^5$ ............................................. C07C 69/96
[52] U.S. Cl. ...................................... 558/264; 558/263
[58] Field of Search ................. 558/264, 263, 265; 560/302

[56] References Cited

U.S. PATENT DOCUMENTS 4,097,408  6/1978  Sanchez ...................... 526/228

FOREIGN PATENT DOCUMENTS 54-107994  8/1979  Japan .
58-83008   5/1983  Japan .
61-231005 10/1986  Japan .
3-174460   7/1991  Japan .

Primary Examiner—Joseph L. Schofer
Assistant Examiner—Jeffrey T. Smith
Attorney, Agent, or Firm—Oblon, Spivak, McClelland, Maier & Neustadt

[57] ABSTRACT

An organic peroxide consisting of 1 to 30 repeating units represented by the formula

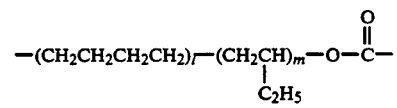

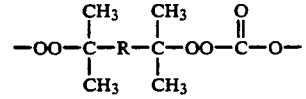

wherein R stands for one group selected from the class consisting of ethylene, acetylene, cyclohexylene, and phenylene groups and one of l and m stands for an integer of at least 1 and l+m stands for an integer in the range of from 6 to 220. Polymerization initiator for a vinyl monomer consisting of the organic peroxide mentioned above. A method for polymerizing a vinyl monomer by using the polymerization initiator mentioned above.

12 Claims, No Drawings

ORGANIC PEROXIDE AND USE THEREOF

BACKGROUND OF THE INVENTION

1. Field of the Invention

This invention relates to a novel organic peroxide, use of the organic peroxide as a polymerization initiator, and a method for the polymerization of a monomer by the use of said organic peroxide as a polymerization initiator. More particularly, a high molecular polymer can be obtained with high efficiency by polymerizing a vinyl monomer in the presence of the organic peroxide as a radical polymerization initiator for the vinyl monomer. The polymer thus obtained has high strength and excels in flexibility and flowability. This invention further relates to a method for polymerization which is characterized by using the organic peroxide as a polymerization initiator.

2. Description of the Prior Art

The use of polymer materials in a wider range of fields in recent years has created a demand for polymers possessing various physical properties. It is known to the art that radical polymerization of a monomer effected by the use of a special initiator produces a modified polymer. As initiators of this sort, such polyfunctional polymerization initiators as 1,1-bis(t-butylperoxy)cyclohexane (Japanese Patent Public Disclosure SHO 54(1979)-107994, tris(t-butyl-peroxy)triazine (Japanese Patent Public Disclosure SHO 58(1983)-83008, and tri-t-butyl ester of pertrimellitic acid (Japanese Patent Public Disclosure SHO 61(1986)-231005 and such polymeric polymerization initiators as polyperoxy phthaloyl ["Journal of Industrial Chemistry", vol. 69, page 718 (1966)] have been disclosed. Further, Japanese Patent Public Disclosure HEI 3(1991)-174460 discloses modification of a resin by the use of a low-temperature decomposition type diacyl type organic peroxide possessing a repeating unit represented by the formula (1):

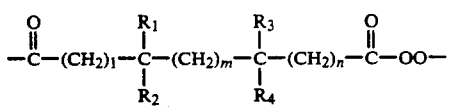

(1)

(wherein l and n independently stand for an integer in the range of 1 to 20, m stands for 0 or an integer in the range of 1 to 5, and $R_1$, $R_2$, $R_3$ and $R_4$ independently stand for a hydrogen atom or an alkyl group of 1 to 5 carbon atoms, a cyclohexyl group, or a phenyl group).

To be specific, it is known that the use of such an initiator as 1,1-bis(t-butylperoxy)-cyclohexane enables a monomer to give rise to a polymer improved in resistance against heat and shock and that the use of an initiator such as tris(t-butyl-peroxy)triazine or tri-t-butyl ester of trimellitic acid enables production of a polymer having a backbone of the shape of a pentacle and exhibiting high strength and ideal flowability. It is further known that an attempt is being made to produce a block polymer possessing new physical properties by the use of such polymeric initiators as polyperoxy phthaloyl and that the use of a low-temperature decomposition type diacyl-based organic peroxide possessing a special structure enables production of a polymer with improved in brittle fracture behavior and strength which can resist repeated shocks.

In recent years, however, polymers have been put to a wider range of uses In many cases the quality required of the article shaped from the polymer has reached the point where the conventional method used for the production of the shaped article is no longer satisfactory. For the enhancement of the mechanical strength of a polymer, for example, it is known to use a method for giving the polymer an increased molecular weight by the use of such a special initiator as described above. Generally, however, the polymer produced suffers from degraded formability. In other words, a polymer which enjoys high mechanical strength and, at the same time, excels in formability cannot be obtained by merely increasing the molecular weight of the polymer. Even in the case of the method disclosed in Japanese Patent Public Disclosure HEI 3(1991)-174460, the effect cannot be called fully satisfactory in light of the severe requirements of the market. It is desired to develop a polymer which excels in formability and moreover enjoys higher mechanical strength than that of the conventional polymer and to perfect a polymerization initiator capable of enabling production of such an improved polymer.

SUMMARY OF THE INVENTION

The present inventors made a study with a view to developing a polymer which meets the requirements mentioned above and, consequently, succeeded in synthesizing a novel organic compound which enables highly efficient production of a high molecular weight polymer and serves as a highly useful polymerization initiator in the production of a polymer, particularly a vinyl type polymer, exhibiting high strength and excelling in flexibility and flowability. This invention has been perfected as a result.

To be more specific, this invention relates to an organic peroxide consisting of 1 to 30 repeating units represented by the following formula (2):

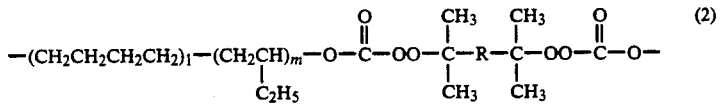

(2)

(wherein R stands for one group selected from the class consisting of ethylene, acetylene, cyclohexylene, and phenylene groups and one of l and m stands for an integer of at least 1 and l+m stands for an integer in the range of 6 to 220), and to a use of the organic peroxide. This organic peroxide is a novel compound not reported in literature.

DESCRIPTION OF THE PREFERRED EMBODIMENT

The organic peroxide of the present invention is obtained by subjecting the hydride of liquid polybutadiene possessing chloroformyloxy groups one each at the opposite terminals of the molecular chain thereof and dihydroperoxide possessing a divalent hydroperoxy group in the molecule thereof to a reaction for removal of hydrogen chloride in the presence of an alkali compound or a tertiary amine at a temperature lower than the decomposition temperature of peroxide bond thereby inducing the formation of a peroxycarbonate bond.

The structure of the terminal groups of the organic peroxide of this invention depends on the stoichiometric ratio of the two reactants to be used in the synthesis. When the hydride of the liquid polybutadiene possessing chloroformyloxy groups at the opposite terminals of the molecular chain thereof is used in an excess amount relative to the dihydroperoxide, for example, the opposite terminals of the resultant organic peroxide are hydroxy groups originating in the chloroformyloxy groups. In the opposite case, the terminals are hydroperoxy groups originating in hydroperoxide.

The hydride of the liquid polybutadiene possessing chloroformyloxy groups at the opposite terminals of the molecular chain thereof to be used for the production of the organic peroxide of this invention is represented by the following formula (3).

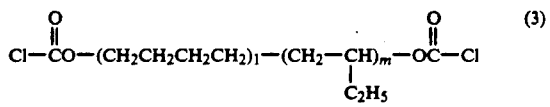

(wherein one of l and m stands for an integer of at least 1 and l+m stands for an integer in the range of 6 to 220). This compound can be obtained by preparing liquid polybutadiene possessing hydroxyl groups one each at the opposite terminals of the molecular chain thereof by polymerizing butadiene with hydrogen peroxide as an initiator, hydrogenating the liquid polybutadiene, and further converting the hydroxyl groups with phosgene into chloroformyloxy groups. In this case, the liquid polybutadiene described above is obtained as a mixture of a polybutadiene resulting from an additional polymerizing at the 1 and 2 positions of a butadiene and a polybutadiene resulting from an additional polymerizing at the 1 and 4 positions of a butadiene.

The quality of the produced organic compound as a polymerization initiator varies with the mixing ratio of the two kinds of liquid polybutadienes. This means that the physical properties of the polymer obtained by the use of the organic compound as a polymerization initiator are governed by this mixing ratio. This mixing ratio, therefore, is decided in light of the physical properties which the polymer is required to acquire. In the formula (3), one of l and m is required to be an integer of at least one and the ratio of l and m is not subject to any restriction. The average molecular weight of the hydride of the liquid polybutadiene possessing the hydroxyl groups at the opposite terminals of the molecular chain thereof is desired to be in the range of 300 to 12,000, preferably 500 to 9,000. In the formula (3) therefore, l+m stands for an integer in the range of 6 to 220, preferably 9 to 160. If this molecular weight is less than 300, fully satisfactory physical properties cannot be imparted to the produced polymer Conversely, if the molecular weight exceeds 12,000, the synthesis of the organic peroxide of this invention is difficult to achieve and, as a result, the synthesis suffers from poor yield.

The dihydroperoxide containing a divalent hydroperoxy group in the molecule thereof and used for the production of the organic peroxide of this invention is represented by the following formula (4):

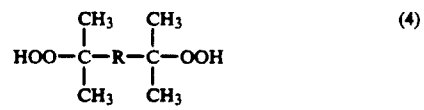

(wherein R stands for one member selected from the class consisting of ethylene, acetylene, cyclohexylene, and phenylene groups).

The dihydroperoxides which are effectively usable herein include 2,5-dimethyl-2,5-dihydroperoxy hexane, 2,5-dimethyl-2,5-dihydroperoxy hexine-3, 1,3-bis(1-hydroperoxy-1-methylethyl) cyclohexane, 1,4-bis(1-hydroperoxy-1-methylethyl) cyclohexane, 1,3-diisopropyl benzene dihydroperoxide, 1,4-diisopropyl benzene dihydroperoxide, and mixtures thereof, for example.

The alkali compounds which are useful for the synthesis of the organic peroxide of this invention are inorganic bases such as, for example, NaOH, KOH, LiOH, and $Na_2CO_3$. The tertiary amines which are similarly useful are pyridine, triethyl amine, and tributyl amine, for example.

The synthesis can be carried out in a solvent The solvents which are effectively usable for this synthesis are halogenated hydrocarbons (such as, for example, chloroform and carbon tetrachloride), aromatic hydrocarbons (such as, for example, benzene, toluene, and ethyl benzene), and aliphatic hydrocarbons (such as, for example, hexane, octane, petroleum ether, and mineral spirit). The reaction temperature is not higher than the temperature at which the hydroperoxy group is decomposed. It is generally in the approximate range of $-10°$ C. to $+40°$ C.

The number of repeating units of the formula (2) in the organic peroxide of this invention (hereinafter referred to as "average condensation degree") is in the range of 1 to 30, preferably 2 to 20. If the average condensation degree exceeds 30, the synthesis of the organic peroxide is difficult to achieve.

In the formula (2), R stands for one group selected from the class consisting of ethylene, acetylene, cyclohexylene, and phenylene groups.

The reason for the particular structure is that the organic peroxide possessing this structure exhibits a high activity as a polymerization initiator. Particularly, the organic peroxide which has a cyclohexylene group or a phenylene group as R is characterized by manifesting high solubility in the solvent and the aromatic monomer. Further, suitable selection of a group for R allows subtle variation of the physical properties of the polymer produced by the polymerization. When an ethylene group or a cyclohexylene group is selected for R, for example, the polymer enjoys enhanced flowability. When an acetylene group or a phenylene group is selected for R, the polymer acquires superior strength.

The organic peroxide of this invention is such that the structure thereof can be confirmed from its infrared absorption spectrum and nuclear magnetic resonance spectrum. The peroxy group content of the organic peroxide can be determined from the amount of active oxygen found by iodometry.

The organic peroxide of this invention is useful as a radical polymerization initiator for a vinyl monomer. The vinyl monomers which are suitable for radical polymerization include olefins such as ethylene, propylene, styrene, α-methyl styrene, and chlorostyrene, diolefins such as butadiene, isoprene, and chloroprene, vinyl esters such as vinyl acetate and vinyl propionate, unsaturated nitriles such as acrylonitrile and methacrylonitrile, acrylic acid and methacrylic acid and esters and amides thereof, halogenated vinyl compounds and halogenated vinylidene compounds such as vinyl chloride, vinyl bromide, vinyl fluoride, vinylidene chloride, and vinylidene fluoride, perhaloolefins such as ethylene tetrafluoride, vinyl ethers such as methyl vinyl ether and butyl vinyl ether, and mixtures thereof such as, for example, styrene -methyl methacrylate, α-methyl styrene-acrylonitrile, and acrylonitrile-butadiene-styrene.

The polymerization using the organic peroxide of this invention as a initiator can be reliably effected by any of the conventional methods such as bulk polymerization, suspension polymerization and solution polymerization.

The amount of the organic peroxide of this invention to be added to the monomer, though suitable fixed in accordance with the desired speed of polymerization and the physical properties desired of the produced polymer, generally falls in the range of 0.00001 to 100 parts by weight, preferably 0.0001 to 10 parts by weight, as pure substance based on 1 part by weight of the vinyl monomer to be polymerized.

The temperature of the polymerization effected by the use of the organic peroxide of this invention is in the range of from 40° C. to 180° C., preferably from 60° C. to 160° C. If the polymerization temperature is lower than 40° C., the polymerization proves to be economically disadvantageous in the sense that the speed of polymerization is unduly low. Conversely, if the polymerization temperature exceeds 180° C., the service life of the polymerization initiator is unduly short and high conversion of polymerization is difficult to achieve.

The organic peroxide of this invention can be used either by itself or in combination with another polymerization initiator. The other polymerization initiator adopted for the combination can be suitably selected from among conventional polymerization initiators such as, for example, other organic peroxides and azo compounds. Such factors as the amount of the other polymerization initiator to be used can be suitably fixed according to the desired polymerization speed and the physical properties expected of the produced polymer.

The organic peroxide of this invention is a novel compound and is useful as an initiator of the polymerization of various vinyl monomers such as styrene and methacrylic ester for efficient production of a high molecular weight vinyl polymer Since this polymerization initiator is capable of introducing a long chain aliphatic saturated hydrocarbon backbone represented by a specific structural formula into the produced polymer, it allows the produced polymer to acquire high strength and enjoy improvement in flexibility and flowability.

The polymer thus obtained can be used as an agent for curbing shrinkage during the setting of an unsaturated polyester or as an agent for imparting compatibility to a polymer alloy.

Now, this invention will be described more specifically with reference to working examples and comparative experiments. Regarding the hydride of liquid polybutadiene possessing chloroformyloxy groups one each at the opposite terminals of the molecular chain thereof and used as a raw material in the following examples of synthesis of an organic peroxide, the average molecular weight of the hydride was calculated from the average molecular weight determined on the basis of the hydroxyl value of the hydride of the liquid polybutadiene having hydroxyl groups one each at the opposite terminals of the molecular chain thereof and used for the sake of chloroformylation. The molecular weight of the produced organic peroxide was determined by GPC. The calibration curve used for the calculation of the molecular weight was prepared by using as the standard specimen the hydride of a known molecular weight of liquid polybutadiene possessing hydroxyl groups one each at the opposite terminals thereof.

SYNTHESIS OF ORGANIC PEROXIDE

Example 1

In a four-neck flask having an inner volume of 500 ml and fitted with a stirring device and a thermometer was placed a liquid mixture consisting of 4.3 g (0.024 mol) of 2,5-dimethyl-2,5-dihydroperoxy hexane, 69.7 g (0.03 mol) of the hydride of liquid polybutadiene possessing chloroformyloxy groups one each at the opposite terminals of the molecular chain thereof (average molecular weight 2325), and 140 g of chloroform. The contents of the flask were stirred and the temperature thereof was kept at 30° C., 9.5 g (0.012 mol) of pyridine was added dropwise thereto, and the reactants were left reacting at normal room temperature for six hours following the completion of the dropwise addition of pyridine. After the reaction was completed, the reaction solution was washed twice with 250 ml of an aqueous 5% hydrochloric acid solution to remove excess pyridine, washed once with an aqueous 5% NaOH solution, and washed with water until neutralized. The neutral reaction solution obtained was dehydrated with anhydrous sodium sulfate and anhydrous magnesium sulfate, suction filtered, and subsequently concentrated under a vacuum. Consequently, 59.9 g of a viscous liquid of a light gray color was obtained The average molecular weight of this compound determined by GPC was 11,900. By calculation, the average condensation degree of this compound was found to be 4.0. This substance was identified by the IR and the $^1$H-NMR spectrum. In the IR spectrum, carbonyl absorptions by the peroxy carbonate compound were found at 1750 cm$^{-1}$ and 1792 cm$^1$. Further, in the $^1$H-NMR spectrum, the proton peaks of a methylene group and a methyl group belonging to the hydride of liquid polybutadiene were found respectively at $\delta=1.24$ and $\delta=0.84$. On the basis of the average condensation degree and the proton ratio of the $^1$H-NMR spectrum, the compound was found to possess the following structure.

$$\text{HO}-\text{R}_5\text{-}\!\!\left(\text{O}-\overset{\text{O}}{\underset{\|}{\text{C}}}-\text{OO}-\underset{\underset{\text{CH}_3}{|}}{\overset{\overset{\text{CH}_3}{|}}{\text{C}}}-\text{CH}_2-\text{CH}_2-\underset{\underset{\text{CH}_3}{|}}{\overset{\overset{\text{CH}_3}{|}}{\text{C}}}-\text{OO}-\overset{\text{O}}{\underset{\|}{\text{C}}}-\text{O}-\text{R}_5\right)_{\!\!4.0}\!\!\text{OH} \quad (5)$$

(wherein R$_5$ stands for 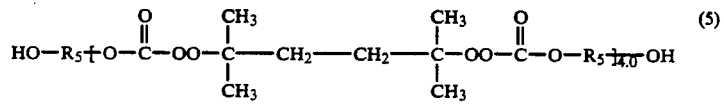)

By the determination using iodometry, the active oxygen content of this compound was found to be 1.05%. By calculation, the purity of the compound was found to be 97.8% and the yield thereof to be 81.5%.

Examples 2 to 5

Organic peroxides conforming to the present invention were synthesized by repeating the procedure of Example 1, except that the amount of dihydroperoxide used for the synthesis was varied. In the IR spectra obtained of the products of synthesis, carbonyl absorptions of peroxycarbonate compounds were found. Further, the $^1$H-NMR spectra of these compounds showed proton peaks of a methylene group and a methyl group belonging to each of the hydrides of liquid polybutadiene. The data such as constitutional formulas, amounts obtained, average molecular weights, average condensation degrees, active oxygen contents, purities, and yields of the products of synthesis are shown in Table 1.

TABLE 1

| | Hydroperoxide | | Constitutional formula | Average molecular weight | Amount obtained (%) | Active oxygen content | Purity (%) | Yield (%) |
|---|---|---|---|---|---|---|---|---|
| | Name of compound | Amount used | | | | | | |
| Example 2 | 2,5-Dimethyl-2,5-dihydroperoxy hexane | 4.8 g (0.027 mol) | HO—R$_5$—O—C—OO—C—CH$_2$—CH$_2$—C—OO—C—O—R$_5$—OH (with CH$_3$ groups), n=9.1 | 24300 | 55.8 | 1.12% | 93.5 | 72.1 |
| Example 3 | 2,5-Dimethyl-2,5-dihydroperoxy hexine-3 | 5.2 g (0.030 mol) | HO—R$_5$—O—C—OO—C—C≡C—C—OO—C—O—R$_5$—OH (with CH$_3$ groups), n=16.8 | 43000 | 45.4 | 1.19% | 95.1 | 59.3 |
| Example 4 | 1,4-Bis(1-methyl-1-hydroperoxy ethyl)cyclohexane | 5.6 g (0.024 mol) | HO—R$_5$—O—C—OO—C(CH$_3$)$_2$—[cyclohexane]—C(CH$_3$)$_2$—OO—C—O—R$_5$—OH, n=4.1 | 12400 | 37.7 | 1.01% | 95.3 | 49.1 |
| Example 5 | 1,3-Diisopropyl benzene di-hydroperoxide | 5.4 g (0.024 mol) | HO—R$_5$—O—C—OO—C(CH$_3$)$_2$—[benzene]—C(CH$_3$)$_2$—OO—C—O—R$_5$—OH, n=4.2 | 12600 | 47.1 | 1.02% | 95.7 | 61.7 |

$R_5 = -(CH_2CH_2CH_2CH_2)_{25.0}-(CH_2-CH_2)_{33.7}-$
                                          |
                                        $C_2H_5$

Example 6

An organic peroxide of this invention was synthesized by following the procedure of Example 1, except that the hydride of liquid polybutadiene possessing chloroformyloxy groups one each at the opposite terminals of the molecular chain thereof (average molecular weight 785) was used in the amount of 23.5 g (0.030 mol). As a result, 20.5 g of a viscous liquid of a light gray color was obtained. In the IR spectrum obtained of the product of synthesis, carbonyl absorptions of the peroxycarbonate compound were found. Further in the $^1$H-NMR spectrum obtained of the compound, proton peaks of a methylene group and a methyl group belonging to the hydride of liquid polybutadiene were found. The average molecular weight of this compound was 4100. By calculation, the average condensation degree of this compound was found to be 3.9. By analyzing the proton ratio in the $^1$H-NMR spectrum and the average condensation degree, this compound was found to possess the following structure.

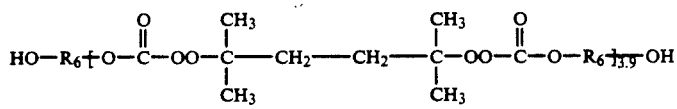

(wherein $R_6$ stands for $-(CH_2CH_2CH_2CH_2)_{1.5}-(CH_2-CH\!\!-\!\!)_{9.7}$
                                                                   |
                                                                 $C_2H_5$)

By means of iodometry, the active oxygen content of this compound was found to be 2.91%, the purity thereof to be 96.3%, and the yield thereof to be 77.0%.

Example 7

A polymerization initiator conforming to this invention was synthesized by following the procedure of Example 1, except that the hydride of liquid polybutadiene possessing chloroformyloxy groups one each at the opposite terminals of the molecular chain thereof (average molecular weight 8,925) was used in the amount of 267.7 g (0.030 mol). As a result, 120.7 g of a viscous liquid of a light gray color was obtained. In the IR spectrum obtained of the product of synthesis, carbonyl absorptions of the peroxycarbonate compound were found. Further, in the $^1$H-NMR spectrum obtained of this compound, proton peaks of a methylene group and a methyl group belonging to the hydride of liquid polybutadiene were found. The average molecular weight of this compound was found to be 44,900. By calculation, the average condensation degree of this compound was found to be 4.0. By the analysis of the proton ratio in the $^1$H-NMR spectrum and the average condensation degree, this compound was found to have the following structure.

By means of iodometry, the active oxygen content of this compound was found to be 0.27%, the purity thereof to be 94.8%, and the yield thereof to be 42.4%.

The organic peroxides synthesized in the examples cited above were each used as a polymerization initiator in polymerizing a monomer. The mol number of each of the initiators thus used was reported in the mol number of a relevant peroxide bond.

POLYMERIZATION OF STYRENE

Example 8

In a four-neck flask having an inner volume of 3,000 ml, a solution prepared by adding 16.9 g (0.011 mol) of the organic peroxide synthesized in Example 1 as a polymerization initiator to 1,500 g of styrene and 500 g of ethylbenzene was placed and heated under an atmosphere of nitrogen gas at 110° C. for 10 hours to effect solution polymerization of styrene. Then, the reaction product was diluted by addition of ethylbenzene and the polymer in the diluted reaction product was refined twice by re-precipitation using methanol as a re-precipitation solvent. The conversion of polymerization determined on the basis of the dry weight of the produced polymer was 78.9%. By means of GPC, the weight average molecular weight of the polymer was found to be 358,000. The structure of this polymer was confirmed by $^1$H-NMR. As a result, it was confirmed that a methyl group belonging to the hydrocarbon backbone of the organic peroxide used as the polymerization initiator was present in the polymer and the long-chain hydrocarbon backbone was clearly introduced in polystyrene. By calculation based on the analysis of the $^1$H-NMR spectrum, the ratio of introduction of the long-chain hydrocarbon backbone was found to be 1.2% by weight.

Further, the polymer was tested for physical properties as shown below. The results are shown in Table 2.

Determination of Mechanical Properties

Test pieces 12.62 mm in width and 3.08 mm in thickness were prepared by compressing a given polymer with a cold press and forming the compressed polymer with an injection molder. These test pieces were used for the determination of the following mechanical properties. The results are shown in Table 2.

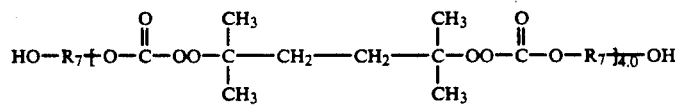

(wherein $R_7$ stands for $-(CH_2CH_2CH_2CH_2)_{20.2}-(CH_2-CH\!\!-\!\!)_{136.3}$
                                                                    |
                                                                  $C_2H_5$)

Tensile Test

This test was carried out at 23° C. in accordance with the procedure specified in JIS K-7113 with necessary modifications. The stretch speed was 5 mm/min and the distance between the chucks was 115 mm.

was used instead as a polymerization initiator. As a result, a polymer having a weight average molecular weight of 360,000 was obtained. Test pieces of the polymer were prepared in the same manner as in Example 8 and used for the determination of physical properties. The results of polymerization and the results of the tests are shown in Table 2.

TABLE 2

| | Polymerization initiator | Amount of initiator used *1 | Conversion % | Mw | Ratio of introduction (wt %) *2 | Tensile Test Elongation % | Tensile Test Strength kg/mm² | Bending Test Flexure mm | Bending Test Strength kg/mm² | Melt flow rate g/10 min |
|---|---|---|---|---|---|---|---|---|---|---|
| Example 8 | Organic peroxide synthesized in Example 1 | 16.9 (0.011) | 78.9 | 358000 | 1.2 | 3.8 | 5.23 | 6.6 | 10.1 | 3.0 |
| Example 9 | Organic peroxide synthesized in Example 2 | 15.9 (0.011) | 77.5 | 354000 | 1.0 | 3.5 | 5.21 | 6.4 | 10.1 | 2.9 |
| Example 10 | Organic peroxide synthesized in Example 5 | 17.4 (0.011) | 80.1 | 340000 | 1.1 | 3.5 | 5.20 | 6.5 | 10.1 | 3.3 |
| Example 11 | Organic peroxide synthesized in Example 6 | 6.8 (0.011) | 78.5 | 355000 | 0.4 | 2.6 | 5.20 | 6.0 | 10.1 | 2.5 |
| Example 12 | Organic peroxide synthesized in Example 7 | 65.8 (0.011) | 77.9 | 360000 | 4.5 | 4.9 | 5.24 | 7.3 | 10.2 | 3.5 |
| Comparative Experiment 2 | Bu-I *3 | 1.1 (0.011) | 68.2 | 360000 | — | 1.6 | 5.19 | 5.4 | 10.0 | 1.4 |

*1: Value relative to 1,500 g of styrene. The numeral in the parenthese ( ) is the mol number of peroxide bond.
*2: Ratio of introduction of long-chain saturated hydrocarbon backbone in polystyrene.
*3: t-Butyl peroxy isopropyl carbonate.

Bending Test

This test was carried out at 23° C. in accordance with the procedure specified in JIS K-7203. The bending speed was 1.5 m m/min and the distance between the supporting points was 50 mm.

Melt Flow Rate

The test for this property was carried out in accordance with the procedure specified in JIS K-7210 with necessary modifications. The test temperature was 200° C. and the load was 5 kgf.

Examples 9 to 12

Solution polymerization of styrene was carried out by following the procedure of Example 8, except that the organic peroxides of this invention synthesized in Examples 2, 5, 6, and 7 were respectively used as a polymerization initiator in place of the organic peroxide synthesized in Example 1. The polymers obtained by the synthesis were refined in the same manner as in Example 8. Test pieces of these polymers were prepared in the same manner as in Example 8 and used for the determination of physical properties. The results of polymerization and the results of physical property tests are shown in Table 2.

Comparative Experiment 1

Solution polymerization of styrene was carried out by following the procedure of Example 8, except that 1.9 g (0.011 mol) of t-butyl peroxy isopropyl carbonate was used as a polymerization initiator in place of the polymerization initiator of this invention. As a result, polystyrene having a weight average molecular weight of 285,000 was obtained at a conversion of 75.0%.

Comparative Experiment 2

Solution polymerization of styrene was carried out by following the procedure of Example 8, except that 1.1 g (0.008 mol) of t-butyl peroxy isopropyl carbonate As shown above, the polymerization initiators of this invention, when added in a fixed mol number, enabled production of polymers of higher molecular weights than other initiators. Further, as shown in Table 2, the polymers produced by the use of the initiators of this invention acquired improved mechanical properties, i.e. excellent flexibility manifested in the form of elongation and flexure, in spite of high strength, in response respectively to the impacts of stretching and bending and, at the same time, ideal flowability, as compared with the other polymers of the same molecular weight.

POLYMERIZATION OF METHYL METHACRYLATE

Example 13

In a glass ampoule having an inner volume of 20 ml was placed 10 ml of a sample solution prepared by adding 31.4 g (0.020 mol) of the organic peroxide of this invention synthesized in Example 5 as a polymerization initiator to 60 g of methyl methacrylate and 40 g of benzene. This ampoule now containing the sample solution was evacuated to a vacuum and sealed by fusion. It was then kept in a constant temperature oil bath at 100° C. for five hours to effect polymerization of methyl methacrylate. Then, the reaction product was removed from the ampoule and tested by the internal standard method using gas chromatography to determine the unaltered monomer content and calculate the conversion of polymerization. As a result, the conversion of polymerization was found to be 98.5%. Further, the reaction product was diluted by addition of benzene and the polymer in the diluted product was refined twice by subjecting the diluted product to the method of re-precipitation using methanol as a re-precipitation solvent. By GPC, the average molecular weight of this produced polymer was found to be 100,000. The structure of the polymer was confirmed by means of ¹H-

NMR. As a result, it was confirmed that a methylene group and a methyl group belonging to the hydrocarbon backbone were present in the organic peroxide and that a long-chain aliphatic hydrocarbon backbone was introduced in the methyl methacrylate. By calculation based on the analysis of the $^1$H-NMR spectrum, the ratio of introduction of the long-chain hydrocarbon backbone was found to be 5.1% by weight.

The polymer was further tested for physical properties as follows.

Production of Film with Polymer

The polymer mentioned above was dissolved in toluene and the polymer solution was applied to a bonderized sheet 50 mm in width, 150 mm in length, and 0.3 mm in thickness (produced by Test Panel Corp.). The applied layer of the solution was dried with air and treated with a drier to expel toluene to obtain a test sheet.

Determination of Quality of Film

The test sheet was subjected to a bending test. This bending test was carried out by a tester keeping firm hold of the opposite ends of the test sheet, bending the test piece, and visually examining the test piece to determine the extent to which the applied film of the polymer separated from the bonderized sheet. It was found that the film showed no sign of separation, crack, or blush.

Comparative Experiment 3

Solution polymerization of methyl methacrylate was carried out by following the procedure of Example 13, except that 2.6 g (0.015 mol) of t-butyl peroxy isopropyl carbonate was used as a polymerization initiator in place of the polymerization initiator of this invention. The polymer thus obtained was refined in the same manner as in Example 13. In this case, the conversion of polymerization was found to be 95.9%. The weight average molecular weight of this polymer was found to be 100,000. A test sheet coated with the polymer was prepared by following the procedure of Example 13 and subjected to a bending test. As a result, the film was observed to sustain cracks.

What is claimed is:

1. An organic peroxide consisting of 1 to 30 repeating units represented by the formula:

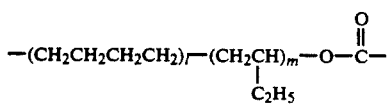

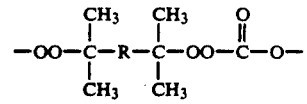

wherein R stands for one group selected from the class consisting of ethylene, acetylene, cyclohexylene, and phenylene groups and one of 1 and m stands for an integer of at least 1 and 1+m stands for an integer in the range of from 6 to 220.

2. An organic peroxide according to claim 1, wherein the number of repeating units is in the range of 2 to 20.

3. An organic peroxide according to claim 1, wherein R stands for an ethylene group.

4. An organic peroxide according to claim 1, wherein R stands for an acetylene group.

5. An organic peroxide according to claim 1, wherein R stands for a cyclohexylene group.

6. An organic peroxide according to claim 1, wherein R stands for a phenylene group.

7. Polymerization initiator for a vinyl monomer consisting of an organic peroxide constituted of 1 to 30 repeating units represented by the formula:

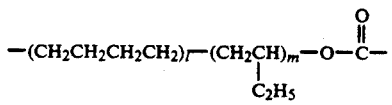

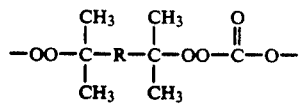

wherein R stands for one group selected from the class consisting of ethylene, acetylene, cyclohexylene, and phenylene groups and one of 1 and m stands for an integer of at least 1 and 1+m stands for an integer in the range of from 6 to 220.

8. Polymerization initiator for a vinyl monomer according to claim 7, wherein the number of repeating units is in the range of 2 to 20.

9. Polymerization initiator for a vinyl monomer according to claim 7, wherein R stands for an ethylene group.

10. Polymerization initiator for a vinyl monomer according to claim 7, wherein R stands for an acetylene group.

11. Polymerization initiator for a vinyl monomer according to claim 7, wherein R stands for a cyclohexylene group.

12. Polymerization initiator for a vinyl monomer according to claim 7, wherein R stands for a phenylene group.

* * * * *